United States Patent [19]

Sawai et al.

[11] 4,203,724
[45] * May 20, 1980

[54] METHOD AND APPARATUS FOR THE MEASUREMENT OF ANTIGENS AND ANTIBODIES

[75] Inventors: Masanobu Sawai, Yamatoshi; Tadamitsu Sudo, Sagamihara; Shogo Enomoto, Tokorozawa, all of Japan

[73] Assignee: Mitsubishi Chemical Industries Limited, Tokyo, Japan

[ * ] Notice: The portion of the term of this patent subsequent to Oct. 3, 1995, has been disclaimed.

[21] Appl. No.: 917,259

[22] Filed: Jun. 20, 1978

Related U.S. Application Data

[63] Continuation-in-part of Ser. No. 825,160, Aug. 16, 1977, Pat. No. 4,118,192.

[30] Foreign Application Priority Data

Aug. 16, 1976 [JP]  Japan ................................. 51/97158
Feb. 14, 1978 [JP]  Japan ................................. 53/15018

[51] Int. Cl.² .................... G01N 21/24; G01N 33/16
[52] U.S. Cl. ................................. 23/230 B; 424/12; 435/7
[58] Field of Search ................. 23/230 B; 424/12; 195/103.5 A; 356/105, 246; 422/55, 56

[56] References Cited

U.S. PATENT DOCUMENTS

| 3,984,533 | 10/1976 | Uzgiris | 23/230 B |
| 4,011,044 | 3/1977 | Uzgiris | 23/230 B |
| 4,118,192 | 10/1978 | Sawai et al. | 195/103.5 A |

FOREIGN PATENT DOCUMENTS

2749956  5/1978  Fed. Rep. of Germany .
1384399  2/1975  United Kingdom .

OTHER PUBLICATIONS

R. J. Cohen, Immunochemistry, 12, pp. 349–351, (Apr. 1975).

*Primary Examiner*—R. E. Serwin
*Attorney, Agent, or Firm*—Oblon, Fisher, Spivak, McClelland & Maier

[57] ABSTRACT

A method of the quantitative measurement of antigens and antibodies by reacting antibody-or antigen-sensitized insoluble carrier particles with a corresponding antigen or antibody or a mixture thereof in a sample and irradiating the reaction mixture with light which contains rays of polychromatic light having a particular wavelength region in the range of 0.6 to 2.4 microns to measure the absorbance or percent absorption of the reaction mixture, and an apparatus for use therein.

27 Claims, 12 Drawing Figures

METHOD AND APPARATUS FOR THE MEASUREMENT OF ANTIGENS AND ANTIBODIES

CROSS-REFERENCE TO RELATED APPLICATIONS

This application is a continuation-in-part of application Ser. No. 825,160 filed Aug. 16, 1977, now U.S. Pat. No. 4,118,192.

BACKGROUND OF THE INVENTION

1. Field of the Invention

This invention relates to a method and apparatus for the measurement of antigens and antibodies. More particularly, this invention relates to a method of the quantitative measurement of antigens and antibodies by reacting an antigen or antibody or a mixture thereof with the corresponding antibody and/or antigen supported on insoluble carrier particles having minute diameters and irradiating the resulting reaction mixture with light of wavelengths in the near infrared for a photometric determination of the antigen or antibody, and an apparatus for use therein.

2. Description of the Prior Art

There is a continuing need for rapid, accurate, qualitative and quantitative determinations of biologically active substances, e.g., antigens, antibodies, at extremely low concentrations. Today, there is a wide need for determining the presence of drugs in body fluids. In addition, in medical diagnosis, it is frequently important to know the presence of various substances which are synthesized naturally by the body or ingested.

Heretofore it has been known to detect antibodies or antigens semiquantitatively by reacting latex particles on which an antibody or an antigen is supported with a corresponding antigen or antibody on a glass plate and observing visually the agglutination state.

In recent years, the qualitative and quantitative analysis of trace amounts of substances, particularly antigens and antibodies, has become increasingly important in various fields, not only in the medical world, but in the fields of biochemistry, hygienics, epidemiology and the like. This invention is directed to the development of a method for use in such determination.

It has been known to detect antigens and antibodies semiquantitatively by reacting an antigen or antibody with a latex particles sensitized with the corresponding antibody or antigen on a glass plate and observing visually the agglutination state of the latex.

In recent years, it was proposed in the following articles to quantitatively determine antigens and antibodies using the above-mentioned latex particles by supporting the corresponding antibody or antigen on the latex particles to sensitize the latex, reacting the supported antibody or antigen with the antigen or antibody to be determined to agglutinate the latex particles, and measuring the rate of decrease in turbidity of the supernatant of the latex by means of visible rays for the determination of the antigen or antibody utilizing the agglutination phenomena of the latex reagent:

(A) CROATICA CHEMICA ACTA, 42, (1970), p.p. 457–466; and (B) European Journal of Biochemistry, Vol. 20, No. 4, (1971), p.p. 553–560.

Since the method of the above proposal utilizes the measurement of rate of decrease in turbidity in order to determine the antigen or antibody, it is necessary to use an antibody- or antigen-sensitized latex of an extremely low concentration, for example, in the range of 0.007 to 0.028%, to carry out the reaction of the latex and the antigen or antibody in a standing state, to remove any impurity capable of affecting the turbidity from the sample to be tested, and the like. As a result, the abovementioned method is disadvantageous in that the rate of the antigen-antibody reaction is inevitably decreased, both the precision and the reproducibility are insufficient for a determination method of antigens or antibodies, and that the removal of impurities sometimes requires extremely complicated operations. Accordingly it is difficult to apply the above method to the determination of such antigens as fibrinogen (Fg), human chorionic gonadotropin (hCG) and the like, since they require complicated procedures for the preparation of their reagent and they do not readily cause reproducible agglutination reactions of the latex if they are present in blood or urine which also contains various other substances capable of adversely affecting the reaction.

Also in the article, (C) Immunochemistry, Vol. 12, p.p. 349–351 (1975)

it was proposed to determine quantitatively antibodies and antigens by irradiating the above-mentioned agglutinated latex particles with a laser beam and measuring the change in width of spectral lines of the scattered light of the laser beam in order to determine the mean diffusion constant (D) which is closely related to the Brownian motion of the agglutinated particles which in turn is inversely proportional to the size of the agglutinated particles. Also in this method, since the antibody- or antigen-sensitized latex is used in a extremely low concentration, for example, as low as 0.001%, the rate of the antigen-antibody reaction is so decreased that both the precision and the reproducibility become poor. In addition, this method is also disadvantageous in that it requires complicated calculation using the technique of spectrum analysis which in turn requires complicated operations, and that any impurity in the sample must be removed prior to the measurement. Accordingly, this method has not been put into practice as well.

The above paper C also describes that the determination of antigens and antibodies by the turbidity method as reported in the foregoing paper A gives extremely imprecise results (FIG. 2 on page 350 of the same). We formerly accomplished an invention which provides a method and apparatus for the rapid determination of antigens and/or antibodies in a sample to be tested with a high precision and a good reproducibility, and proposed it in our copending Japanese Patent Application No. 97158/76 (which is hereinafter referred to as "our prior filed application"). In one aspect, the invention of our prior filed application resides in a method for determining antigens and antibodies by reacting in a liquid medium an antigen or antibody or a mixture thereof with the corresponding antibody and/or antigen which has been supported on insoluble carrier particles having an average diameter of not greater than 1.6 microns and irradiating the resulting reaction mixture with light having a wavelength in the range of 0.6 to 2.4 microns and longer than the average diameter of said carrier particles by a factor of at least 1.5 in order to determine the absorbance of the reaction mixture.

SUMMARY OF THE INVENTION

Upon our further investigation for the purpose of improving the above invention, we have now found that, even if the reaction mixture is irradiated with polychromatic light having a plurality of wavelengths instead of the conventional monochromatic light or similar light monochromated by filtration used in the prior art spectrometry, there is no substantial difference in the results of absorption measurement from that obtained with monochromatic light so that it is possible to determine antigens and antibodies rapidly with a high precision and excellent reproducibility using an irradiating light having a higher intensity and an irradiation unit which does not need to use an expensive, precise light filter or a monschromator. As a result, we have accomplished this invention.

Thus, in accordance with this invention, there is provided a method for determining antigens and antibodies, comprising, reacting an antigen or antibody or a mixture thereof with the corresponding antibody and/or antigen which has been supported on insoluble carrier particles having an average diameter of not greater than 1.6 microns to sensitize the carrier particles, said reaction being carried out in a liquid medium; irradiating the reaction mixture with light which contains rays of polychromatic light having a particular wavelength region in the range of 0.6 to 2.4 microns and so selected that, when applied to the reaction mixture, it gives an increase in absorbance or percent absorption with time; and measuring the absorbance or percent absorption of the reaction mixture for the polychromatic light.

Accordingly, it is an object of this invention to provide a method for determining an extremely minor amount of an antigen and/or antibody which could heretofore be determined practically only by the radioimmunoassay (RIA) method, with a precision equal to or higher than that of the RIA method and much more rapidly and safely.

It is another object of this invention to provide a method for the quantitative determination of antigens capable of determining not only multivalent antigens but incomplete antigens such as, for example, haptens.

It is a further object of this invention to provide a method for determining antigens and/or antibodies utilizing not only their agglutination reactions but their inhibitory actions. It is a still further object of this invention to provide a method for rapidly testing whether the concentration of an antigen or antibody in a sample is higher or lower than a certain level, using an extremely small amount of the sample. Other objects and advantages of this invention will become apparent from the following more detailed description of this invention.

BRIEF DESCRIPTION OF THE DRAWING

In FIG. 3: 1; light source; 2: filter; 3: sample cell; 4 reference cell; 5 and 6: photocells; 7: amplifier; 8: recorder.

DETAILED DESCRIPTION OF THE PREFERRED EMBODIMENTS

Figure 1:
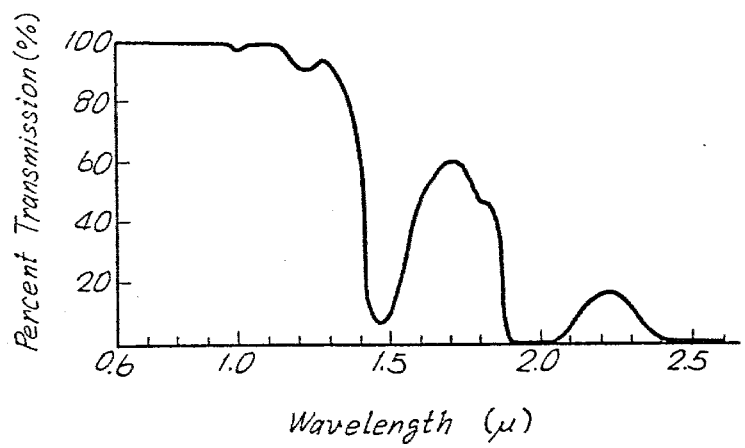
FIG. 1 is a chart of the absorption spectra of water measured with an absorption cell of 1 mm in thickness in the wavelength region of the applied light of 0.6 to 2.4 microns.

As previously mentioned, this invention resides in method for determining antigens and antibodies, comprising, reacting an antigen or antibody or a mixture thereof with the corresponding antibody and/or antigen which has been supported on insoluble carrier particles having an average diameter of not greater than 1.6 microns to sensitize the carrier particles, said reaction being carried out in a liquid medium; irradiating the reaction mixture with light which contains rays of polychromatic light having a particular wavelength region in the range of 0.6 to 2.4 microns and so selected that, when applied to the reaction mixture, it gives an increase in absorbance or percent absorption with time (said applied light being hereinafter referred to as "irradiation light"); and measuring the absorbance or percent abosrption of the reaction mixture for the polychromatic light. Thus, this invention is characterized in that not only monochromatic light or similar monochromated light but also such light as to contain rays of polychromatic light having a substantial wavelength region may be used as the irradiating light in order to take the measurements of absorbance or percent absorption useful for the determination of antigens and antibodies. As previously mentioned, the prior art method in which the degree of agglutination resulting from contact of a sample containing an antigen or antibody or a mixture thereof with latex particles on which the corresponding antibody and/or antigen has been supported (such latex particles being often referred to as "sensitized carrier" or "sensitized latex") is evaluated by the rate of decrease in turbidity of the supernatant of the latex, involves various disadvantages such as poor precision and reproducibility, since the reaction has to be carried out in a standing state with an extremely dilute latex. Also in this prior art method, it is necessary to previously remove any impurity in the sample which may affect the turbidity. In accordance with this invention, contrary to the above prior art method, it is desirable to carry out the reaction of an antigen or antibody in a sample with a sensitized latex in a non-standing state, preferably with active agitation, and the reaction can be effected with a sensitized latex at a high concentration.

We have now found that, in order to detect quantitatively the degree of the reaction between an antigen or antibody in a sample and the corresponding antibody or antigen supported on microparticles of an insoluble carrier, it is remarkably effective:

(1) to use an insoluble carrier having an average particle diameter of not greater than 1.6 microns, (2) to irradiate the antigen-antibody reaction mixture with light which contains rays of polychromatic light having a particular wavelength region in the range of 0.6 to 2.4 microns and so selected that, when applied to the reaction mixture, it gives an increase in absorbance or percent absorption with time; and (3) to measure the intensity of the light transmitted by the reaction mixture only for the above-mentioned polychromatic light portion of the irradiating light in order to determine the absorbance or percent absorption of the reaction mixture.

The reason is that the degree of progress or rate of the antigen antibody reaction in the presence of the sensitized microparticles of the insoluble carrier correlates very closely to the absorbance or percent absorption of the reaction mixture measured for the above-mentioned polychromatic light portion of the irradiating light. It is apparent that the rate or degree of progress of the antigen-antibody reaction also correlates to the amount (or concentration) of the antibody and/or antigen in the sample as long as the reaction is carried out under predetermined, substantially fixed conditions. The above-mentioned method according to this invention, therefore, permits rapid determination of an antigen and/or antibody in a sample with an extremely high precision by a technique quite different from the measurements of turbidity and mean diffusion constant as employed in the prior art methods. As previously mentioned, the irradiating light used in this invention is light containing rays of polychromatic light which has a particular wavelength region in the range of 0.6 to 2.4 microns and which, when applied to the reaction mixture to be tested, gives an increase in absorbance or percent absorption with time.

It has now been found that, when an antigen or antibody in a sample is reacted with a latex of insoluble carrier particles having an average diameter of not greater than 1.6 microns which has been sensitized with the corresponding antibody or antigen, the agglutination of the sensitized latex proceeds concomitantly with the progress of the antigen-antibody reaction at least in the former stage of the course of the reaction, particularly in its relatively early period, and that, when the reaction mixture is irradiated with light which contains rays of polychromatic light having an appropriate wavelength region in the range of 0.6 to 2.4 microns, the absorbance or percent absorption of the reaction mixture measured for the polychromatic light portion of the irradiation light in turn increases concomitantly with the progress of the agglutination of the latex.

Accordingly, in the practice of this invention, light of any wavelength region may be used as the irradiating light, as long as it contains rays of polychromatic light having a particular wavelength region in the range of 0.6 to 2.4 microns at which the absorbance or percent absorption of the reaction mixture increases with time as the reaction proceeds. Also in the practice of this invention, the light useful for a particular combination of an antigen or antibody in a sample and a sensitized latex can be readily selected by those skilled in the art by making simple preliminary experiments.

Thus, the irradiation light used in the method of this invention has to contain rays of the above-defined polychromatic light, and in some cases it may contain spectral components other than those of the polychromatic light, for example, spectral components of wavelengths beyond the range of 0.6 to 2.4 microns. It is an essential feature of this invention to measure absorbance or percent absorption only for the polychromatic light portion of the irradiation light which has a particular wavelength region in the range of 0.6 to 2.4 microns and which, when applied to the desired reaction mixture, gives an increase in absorbance or percent absorption with time.

Accordingly, if the irradiation light consists essentially of rays of the above-defined polychromatic light, the absorbance or percent absorption of the reaction mixture can be directly measured without any treatment. On the other hand, if the irradiation light contains spectral components other than the above-mentioned polychromatic light rays, the measurement of absorbance or percent absorption may be taken in the following manner:

(i) The light emitted from the light source is previously filtered and only the selected portion of the light which consists essentially of the above-defined polychromatic light rays is then applied as an irradiation light to the reaction mixture in order to measure the absorbance or percent absorption;

(ii) The light emitted from the light source is directly applied to the reaction mixture as an irradiating light, the transmitted light is then filtered and the selected portion of the transmitted light which consists essentially of the above-defined polychromatic light rays is measured to determine the absorbance or percent absorption; or (iii) The light emitted from the source is directly applied to the reaction mixture as an irradiating light, and by the use of a special light sensor which responds substantially only to the above-defined polychromatic light rays, only the portion of the transmitted light which consists essentially of these polychromatic light rays is measured to determine the absorbance or percent absorption.

Thus, the irradiating light may contain spectral components other than the above-defined polychromatic light rays or in other words it may contain spectral components having wavelengths beyond the range of 0.6 to 2.4 microns. However, these spectral components of wavelengths beyond the range of 0.6 to 2.4 microns do not substantially contribute to the measurement of absorbance or percent absorption according to the method of this invention and, in some cases, may cause even an adverse effect such as chemical change of the reaction mixture, elevation of temperature, unexpected luminescence phenomenon or the like. It is generally undesirable, therefore, that the irradiating light contains a considerably large amount of such spectral components having wavelengths beyond the range of 0.6 to 2.4 microns, particularly visible rays of wavelengths shorter than that of blue light and ultraviolet rays. It is advantageous for the irradiating light to be substantially free from rays of wavelengths shorter than 0.6 micron, preferably shorter than 0.8 micron. Rays of wavelengths longer than 2.4 microns tend to cause a rise in temperature of the reaction mixture and therefore it is not desirable for the irradiating light to contain a considerably large amount of these rays. Preferably the irradiating light is substantially free from such rays of longer wavelengths.

Particularly suitable irradiating light for use in this invention is light composed predominantly of rays of polychromatic light having a wavelength region in the range of 0.6 to 2.4 microns, preferably in the range of 0.8 to 1.8 microns.

The polychromatic light useful for this invention may consists of a plurality of rays of substantially monochromatic light, or continuous spectra, or a combination thereof, and it is desirable that the polychromatic light has a wavelength region in the range of 0.6 to 2.4 microns, preferably 0.8 to 1.8 microns and more preferably 0.9 to 1.4 microns. The half width or wavelength range of the polychromatic light is not critical, but it is generally preferable for the polychromatic light to have a half width or wavelength range of at least 0.03 micron, more preferably at least 0.05 micron. As previously described, the method according to this invention is characterized by detecting the change of absorbance or percent absorption with time resulting from the agglutination of the sensitized latex by the use of such polychromatic light as to give an increase in absorbance or percent absorption with time. Accordingly, any polychromatic light which shows such tendency can be used. However, it has now been found that polychromatic light consisting essentially of rays of wavelengths longer than the average diameter of the carrier particles by a factor of at least 1.1, preferably at least 1.5 is particularly favorable for the practice of this invention.

Thus, any light source capable of emitting an irradiating light containing rays of the above-mentioned polychromatic light may be used. Exemplary of the light source are tungsten lamp, xenon lamp, halogen lamp, the Nernst glower, nichrome wire, light emitting diodes (LED), and the like. Of these, the tungsten lamp, halogen lamp, xenon lamp and the Nernst glower which emit continuous spectra over the visible and infrared regions are suitable sources, since an irradiating light of a wide wavelength range, which is substantially free from rays of wavelengths lower than, for example, 0.8 micron can be readily obtained from the light emitted from these sources, merely by passing it through a low pass filter. The light emitting diodes, for example, Ga-As light emitting diode can emit polychromatic light of a peak emission wavelength of about 0.95 micron with a half width of about 50 nm and are particularly favorable sources since the emitted light can directly be used as an irradiating light without further filtration. Heretofore the method of spectroscopic analysis using a ray in the infrared region of wavelengths of at least 2.5 microns or a ray in the ultraviolet region of wavelengths of not greater than 0.4 micron is known as one method for investigating molecular structures or characteristics thereof. The rays in the near infrared or the adjacent visible region in the range of 0.6 to 2.4 microns which is used in this invention and which may hereinafter be referred to as "rays in the near infrared region" for the sake of convenience, however, have heretofore been considered to have only limited uses and therefore attracted little attention.

According to our investigation, it has been found that the above-mentioned rays in the near infrared region in principle possess eligibility as the light to be used in this invention, since they are transmitted very well by aqueous media such as water, aqueous solutions and the like which are used most generally as the basal media for the antigen- or antibody-containing samples such as water, sera, urine, salt solutions, etc., as well as, as the basal media for the above-mentioned latices and among these, particularly the rays in the near infrared wavelengths of from 0.8 to 1.4 microns and from 1.53 to 1.88 microns are absorbed by the aqueous media only to a very little extent.

Any insoluble carrier having an average diameter of not greater than 1.6 microns can be used in this invention. Those insoluble carrier particles having an average diameter greater than 1.6 microns are unfavorable for the determination according to this invention, since a latex containing such particles does not possess a stable uniformity. Preferably the insoluble carrier particles have an average diameter in the range of 0.1 to 1.0 micron, more preferably 0.2 to 0.8 micron, most preferably 0.2 to 0.6 micron. In accordance with this invention, an antigen or antibody in a sample is reacted in the presence of at least liquid medium with insoluble carrier particles having an average diameter in the above-defined range which have been sensitized with the corresponding antibody or antigen (i.e., sensitized carrier) and the reaction mixture is irradiated with the above-mentioned light having an appropriate wavelength region in the range of 0.6 to 2.4 microns after the reaction has been started. In such cases, the rate of increase in absorbance or percent absorption of the reaction mixture for this light is correlated very well to the apparent progress or reaction rate of the antigen-antibody reaction, particularly at an early and middle stages of the reaction, and the apparent progress or rate of the reaction is in turn correlated to the concentration of the antigen or antibody in the sample. On the basis of these principles, therefore, it is possible to determine the concentration of the antigen or antibody in the sample.

The term "percent absorption" used herein is defined by the equation:

$$S = (I_o - I/I_o) \times 100 \, (\%) \tag{1}$$

wherein S represents percent absorption, Io represents the intensity of the transmitted light when the cell contains the same system as the reaction mixture to be measured except for the absence of the antigen and/or antibody, and I represents the intensity of the transmitted light when the cell contains the reaction mixture.

As is apparent from the above definition, the percent absorption used herein may be referred to in another way as the percentage of attenuated or not transmitted light. Since the percent absorption corresponds to absorbance (A) which can be measured by means of a conventional spectrophotometer, for example, for use in infrared spectrometry, it may be expressed in terms of absorbance for the sake of convenience. In the infrared spectrometry, absorbance (A) is defined by the equation:

$$A = \log(I_o/I) \tag{2}$$

wherein Io and I have the same meanings as in Equation (1). Thus, it is possible to determine antigens and antibodies utilizing measurements of either parameter of percent absorption defined by Equation (1) or absorbance by Equation (2). In either course, the results will coincide within an acceptable variation.

In brief the above-mentioned absorbance (A) or percent absorption (S) relates to the relative ratio of Io/I. If the basal medium of the sample is a transparent liquid medium, the measurement of Io may conveniently be performed with only the suspension containing the antibody- or antigen-sensitized insoluble carrier particles, said suspension having been diluted with, for example, water to the same concentration as that in the mixture.

Figure 2:
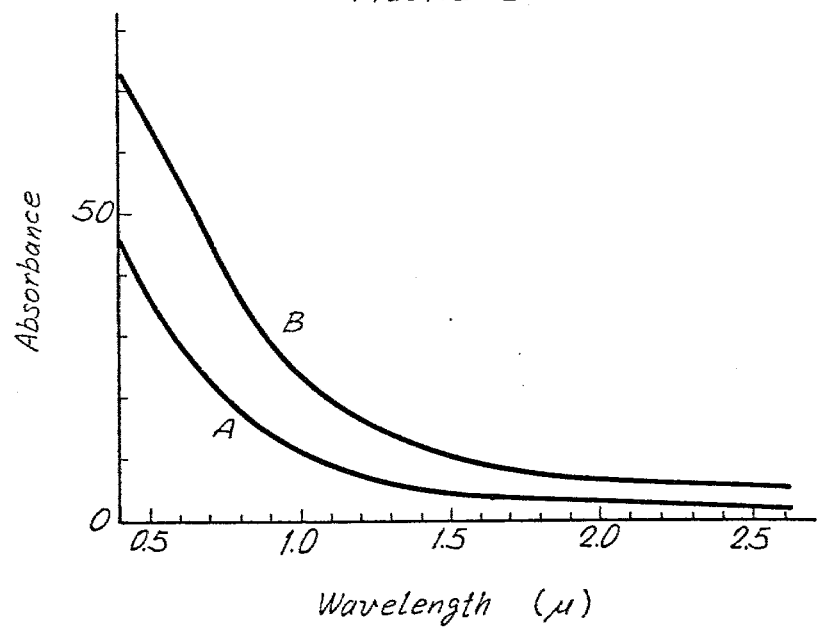
FIG. 2 is a graph which shows the change of absorbance with particle diameter of polystyrene latex.

By the way, percent transmission spectrum in the range of from 0.6 to 2.4 microns of a water layer 1 mm in thickness is shown in FIG. 1, wherein the abscissa indicates the wavelength of light and the ordinate the percent transmission of the light. It can be seen from FIG. 1 that the rays of wavelengths in the range of from 0.6 to 1.4 microns are transmitted by water without substantial absorption by the water which is employed most widely as the basal media for latices and samples, and that the rays of wavelengths in the range of 1.53 to 1.88 microns are also considerably transmitted by water so that the light of wavelengths in these ranges can be utilized in principle in the practice of this invention. Also, it is apparent from FIG. 1 that the rays of wavelengths in the range of 2.1 to 2.35 microns are also transmitted by water in the order of 20%, and therefore it should be understood that the rays of such wavelengths can be used in conjunction with a highly sensitive photometer, although they are rather not preferred. FIG. 2 shows the relationship between the absorbance of a polystyrene latex (1% solids content by weight) in the ordinate and the wavelength of light in microns in the abscissa when a cell of 2 mm in thickness is used. In FIG. 2, Curve A denotes the change in absorbance of a polystyrene latex in which the average diameter of the particles is 0.481 micron and Curve B denotes that of a polystyrene latex in which the average diameter is 0.804 micron. In the determination of abosorbance, the latex was diluted for the convenience of the measurement, and the absorbance of the latex was evaluated by multiplying the actually obtained value of absorbance by the dilution factor.

As will be understood from FIG. 2, the absorbance of the latex is so significantly increased with the rays of wavelengths less than 0.6 micron that it is quite difficult to measure the change in light transmittance or absorbance of an antigen-antibody reaction mixture using a ray of such a wavelength, whereas with the rays of wavelengths of at least 0.8 micron, particularly at least 1 micron, the absorvance of the latex itself is relatively small so that the rays of wavelengths of at least 0.8 micron, preferably at least 1 micron are suitable for the measurement of absorbance or percent absorption.

When Curve A is compared with Curve B in FIG. 2, it is recognized that the absorbance of polystyrene latex increases with increasing average diamter of the polystyrene particles. Accordingly it would also be understood that those latex particles having an excessively large average diameter unfavorable for this invention.

In accordance with our investigation, it has been found that the insoluble carrier particles useful for this invention must have an average particle diameter of not greater than 1.6 microns and that those latex particles having an average diameter of 0.1 to 1 micron, preferably 0.2 to 0.8 micron are suitable.

Figure 5A:
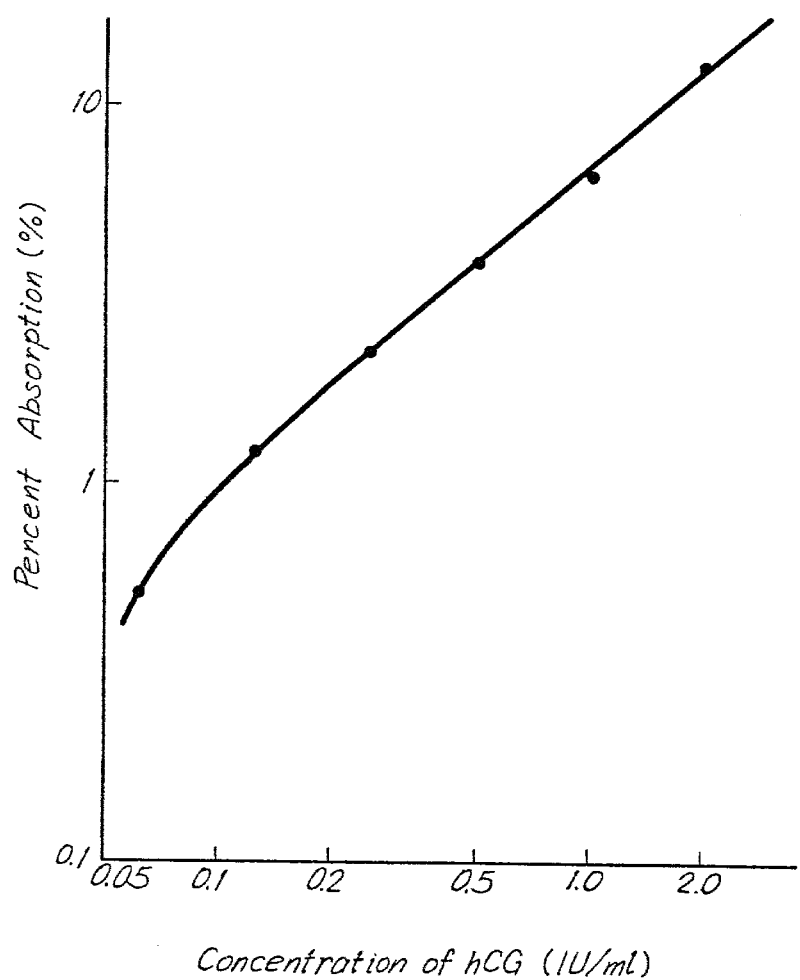
FIG. 5(a) is a calibration curve which shows the change of percent absorption after 2-minutes' reaction with concentration of hCG solution, wherein anti-hCG-latex particles having an average diameter of 0.220 micron are used and a cell is irradiated with polychromatic light emitted from a tungsten lamp as a source, said light being free from any spectral component of wavelength not longer than 0.8 micron.
Figure 6:
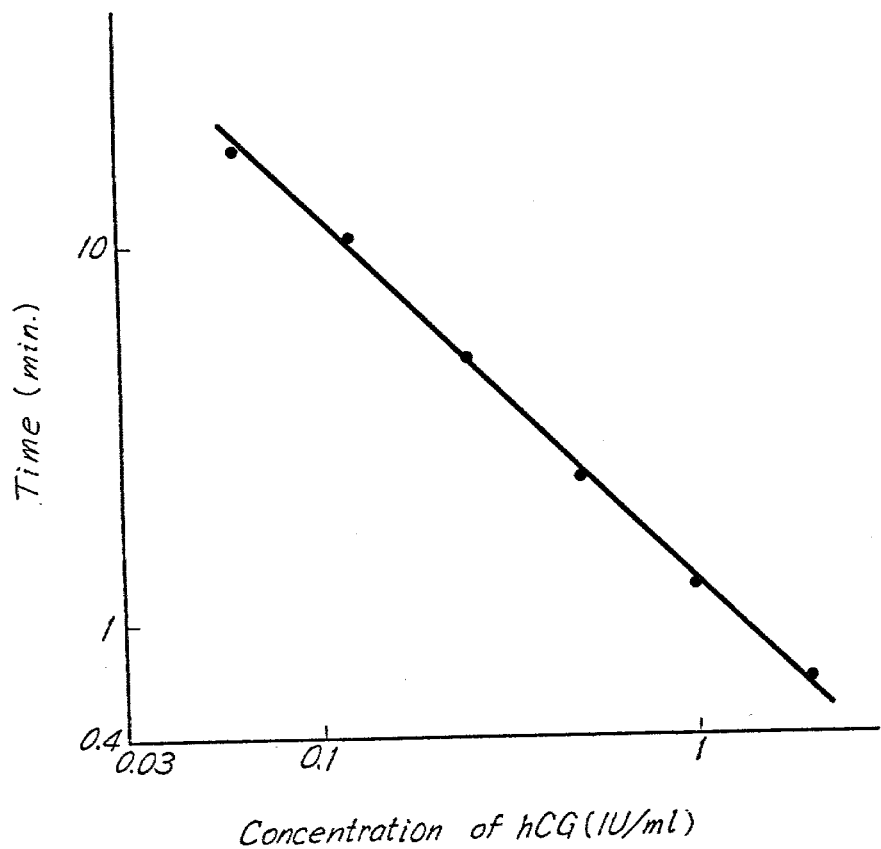
FIG. 6 is a calibration curve which shows the time required to reach 4% absorption, wherein an anti-hCG-sensitized latex reagent is reacted with hCG solutions of various concentrations and a cell is irradiated with light from a tungsten lamp which is free from any spectral component having a wavelength of not longer than 0.8 micron.
Figure 9:
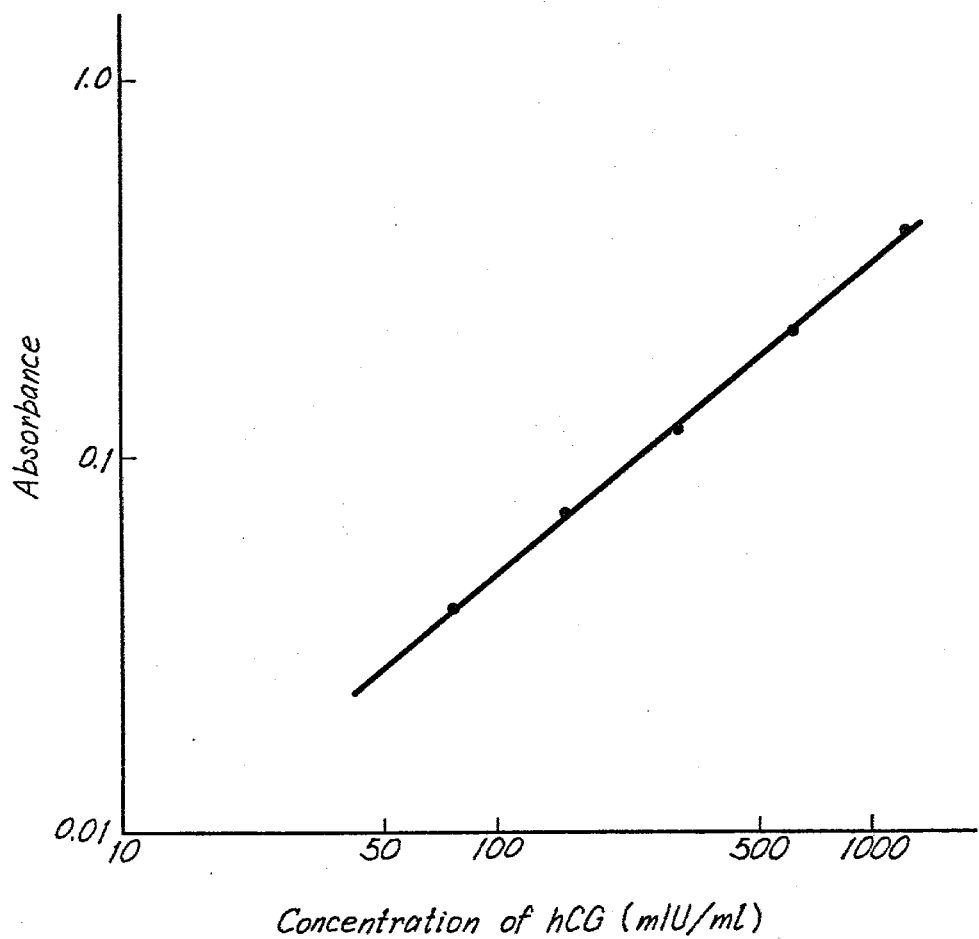
FIG. 9 shows a calibration curve obtained by measuring the percent abosrption of a mixture of an anti-hCG-latex reagent and each of standard hCG solutions at various concentrations with a Ga-As light emitting diode and converting the measured value to absorbance.

Then, FIG. 5(a) (Example 1), FIG. 9 (Example 6) and FIG. 6 (Example 2) are graphs obtained by plotting the relationship between the concentration of an antigen or antibody in a sample and the percent absorption or absorbance after a definite time or the relationship between the time required to a certain value of absorbance or percent absorption and the concentration of an antigen or antibody in a sample, wherein every experiment was made with an irradiating light which contains rays of the above-mentioned polychromatic light. These graphs show extremely good correlation between the absorbance or percent absorption of the reaction mixture and the reaction time (or the progress of the reaction) similar to that evidenced by the example given in our prior application. Accordingly, it should be understood that monochromatic light or similar light need not always be used as the irradiating light and that the determination of antigens and antibodies can be sufficiently effected with polychromatic light. In accordance with this invention, the amount or concentration of an antigen and/or antibody in a sample can be determined by supporting the corresponding antibody and/or antigen on carrier particles (a latex) having the above-defined particle size to prepare a sensitized latex, reacting the antigen and/or antibody in the sample with the sensitized latex, and measuring and evaluating the absorbance or percent absorption of the reaction mixture with rays of a particular wavelength region in the range of 0.6 to 2.4 microns, preferably 0.8 to 1.8 microns and more preferably 0.9 to 1.4 microns.

The insoluble carrier particles useful for this invention include those organic polymer microparticles which are substantially insoluble in the particular liquid medium used for the measurement according to the invention and which have an average diameter within the above-defined range, such as, for example, latices of organic polymers such as polystyrene and styrene-butadiene copolymer obtained by emulsion polymerization; dispersed coccal bacteria such as staphylococci and streptococci, *Bacillus prodigiosus,* rickettsia, cell membrane fragments, etc.; as well as microparticles of inorganic oxides such as silica, solica-alumina and alumina, and finely pulverized minerals, metals and the like. In accordance with the invention, an antibody or antigen which is reactive with the antigen and/or antibody in the sample to be measured is supported on the above-mentioned insoluble carrier particles such as, for example, latex particles (i.e., to sensitize the carrier). For this purpose, the antibody or antigen may be physically and/or chemically adsorbed on the carrier.

Antibodies consist of proteins, whereas antigens are composed of one member selected from various substances such as, for example, proteins, polypeptides, steroids, polysaccharides, lipids, pollen, dust and the like. There have already been proposed a number of methods for supporting these antibodies or antigens, particularly antibodies on insoluble carrier particles.

When an incomplete antigen, particularly a hapten is supported on an insoluble carrier, it is advantageous to chemically modify the carrier with, for example, a coupling agent and subsequently bind the antigen chemically to the modified carrier. If the insoluble carrier used is a latex of a high molecular substance containing functional groups such as sulfo, amino or carboxyl or its reactive derivative group, it is also possible to chemically adsorb the antibody and/or antigen on such latex.

Of the liquid medium useful for this invention, water is the most preferable, although a mixture of water with a water-miscible organic solvent can be used. Exemplary of suitable water-miscible organic solvents are alcohols such as methanol, ethanol, etc.; ketones such as acetone; and the like.

Contrary to the known prior art methods which utilize the measurement of turbidity or the measurement of mean diffusion constant with a laser beam, the method according to this invention provides conditions that enable the insoluble carrier particles sensitized with an antibody or an antigen to react with a corresponding antigen and/or antibody as actively as possible.

On this account, in accordance with the invention, the insoluble carrier particles, for example, latex particles, which are sensitized with an antibody or antigen (hereinafter referred to as "sensitized carrier particles") may be used as a suspension having a concentration of not less than 0.05% by weight, preferably in the range of 0.05 to 1%, more preferably 0.2 to 0.6%. When the concentration of the sensitized carrier particles is much too high, as is apparent from FIG. 2, the transmittance of the suspension itself is so decreased that the measurement of absorbance or percent absorption according to the invention is made difficult. However, in the concentration range in which such a measurement of absorbance or percent absorption is possible, higher concentration of the sensitized carrier particles in the suspension is favorable, whereby it is possible to increase the sensitivity of the quantitative detection of antigens and antibodies. In accordance with the invention, also contrary to the prior art methods, the sensitized carrier particles and the antigen- and/or antibody-containing sample are reacted under non-stationary or non-standing conditions.

For this purpose, the reaction may be advantageously carried out under agitation. Since the reaction is generally carried out in a thin cell, the agitation is conveniently effected for example, by moving a rod vertically or transversely in the cell. Of course, the sensitized carrier particles and the sample may be reacted outside the cell for a certain period of time under predetermined conditions and thereafter the reaction mixture is placed in the cell for the measurement of absorbance or percent absorption. However, in order to make the reaction conditions reproducible, particularly with respect to reaction time in every measurement, the sensitized carrier particles and the sample may be reacted under predetermined, non-standing conditions directly in a cell which has been set in a spectrophotometer, whereby more accurate determination can be achieved by measuring the absorbance or percent absorption.

In this way, the present invention not only makes it possible to determine such a concentration of an antigen and/or antibody in a sample that could heretofore be observed visually in a semiquantitative manner, but enables the determination of an antigen and/or antibody in such a trace amount that could heretofore be determined only by radioimmunoassay (RIA), with a precision equivalent to or higher than that of the RIA method.

In order to determine an antigen and/or antibody in a sample containing an unknown amount of the antigen and/or antibody in accordance with the invention, a set of dilute standard samples are prepared from a standard sample containing a definite amount of the same antigen and/or antibody by diluting it by various factors. Each of the dilute and undiluted standard samples is reacted under predetermined conditions with insoluble carrier particles sensitized with a definite amount of the corresponding antibody or antigen in accordance with the invention, and the absorbance or percent absorption of each reaction mixture is determined to prepare a standard curve for the particular combination of the antigen and/or antibody with the sensitized carrier particles, which indicates the relationship between the amount (concentration) of the antigen or antibody in the standard sample and the absorbance or percent absorption (this type of standard curve being hereinafter referred to as "Standard Curve A" for convenience). Subsequently, an unknown sample to be tested as reacted with the same sensitized carrier particles as that used in the preparation of the standard curve under substantially the same conditions as in the preparation of the standard curve, and the absorbance or percent absorption of the reaction mixture is measured. The amount (or concentration) of the antigen and/or antibody in the unknown sample can be determined by comparing the value of absorbance or percent absorption thus obtained with Standard Curve A.

Alternatively, in the preparation of a standard curve like that described in the above, another standard curve which indicates the relationship between the amount (or concentration) of the antigen or antibody in the standard sample used and the reaction time required to reach a predetermined value of absorbance or percent absorption (this type of standard curve being hereinafter referred to as "Standard Curve B" for convenience) may be prepared. Also in this case, if an unknown sample is reacted with the same sensitized carrier particles under substantially the same conditions as in the preparation of the standard curve, then the amount (or concentration) of the antigen and/or antibody in the unknown sample can be determined by reading the time required to reach the predetermined value of absorbance or percent absorption.

Thus, in accordance with the invention, the amount or concentration of an antigen and/or antibody in an unknown sample may be determined by way of, either (A) the measurement of absorbance or percent absorption of the unknown sample (using Standard Curve A for calibration), or (B) the measurement of the rate of reaction, or the reaction time required for the absorbance or percent absorption to reach a certain value (using Standard Curve B for calibration).

As described previously, the above method (A) is suitable as a determination system with a significantly high precision, not only when the concentration of an antigen and/or antibody in an unknown sample is relatively high, but even if it is so low that it could heretofore be determined only by the RIA method. On the other hand, the above method (B) wherein the reaction rate is measured is suitable for determining a relatively large amount (concentration) of an antigen and/or antibody in an unknown sample, but it is advantageous in that the measurement is quite simple. According to our investigation, Standard Curve A as described above gives in some cases a gentle S-shaped curve rather than a straight line, but no disadvantageous effect is found on the precision of the determination.

The reason why the curve assumes the S-shape as described above is presumed by us to be that the rate of reaction takes part in this shape at lower concentrations of the antigen and/or antibody, whereas the saturation of active sites in the carrier takes part at higher concentrations. It is possible, of course, to enlarge the linear portion in the S-shaped curve by selecting the conditions appropriately in the preparation of the standard curve, and apply substantially only this portion to the determination of unknown samples.

Utilizing the fact that the rate of reaction takes part in the S-configuration of Standard Curve A at lower concentration of an antigen and/or antibody, it is also possible in the practice of this invention to determine an antigen and/or antibody in a sample by reacting it with the corresponding antibody and/or antigen supported on insoluble carrier particles under predetermined substantially fixed conditions and evaluating an increase in absorbance or percent absorption of the reaction mixture for a given period of time after the reaction has been started. Further details of this procedure are given in the specification of our co-pending application filed together with this application and therefore they are not described herein any further. As stated above, the present invention is characterized in that the sensitized carrier particles are advantageously brought into contact with and reacted with a sample at as high a concentration as possible. Therefore, the cell for use in measuring the absorbance or percent absorption of the reaction mixture preferably has a thickness, for example, in the range of 0.5 to 10 mm, more preferably 1 to 5 mm. In order to effect a highly sensitive determination of a trace amount of an antigen or antibody which has heretofore been subjected to the RIA method, it is particularly advantageous:

(a) to use an antigen or antibody having as high an equilibrium constant as possible, (b) to use latex particles, particularly with an average diameter of 0.2 to 0.8 micron, the size distributaion of which should be as narrow as possible, (c) to determine the absorbance or percent absorption with light of wavelengths in the range of 0.8 to 1.8 microns, (d) to select a relatively long reaction time, for example, in the range of a few minutes to one hour or longer, and (e) to increase the concentration of the sensitized latex carrier as long as the absorbance or percent absorption is measurable.

Also, in order to determine an unknown sample accurately in a relatively short time by the measurement of reaction rate (using Standard Curve B), it is advantageous, (f) to use latex particles having a relatively large average diameter, (g) to increase the concentration of the carrier particles in the latex as long as the measurement of absorbance or percent absorption is possible, and (h) to make the period of reaction time relatively short, for example, in the range of 5 seconds to 10 minutes, preferably 10 seconds to 3 minutes.

In this case, when the time required to reach a predetermined value of absorbance or percent absorption is plotted as the ordinate and the concentration as the abscissa, both on a log scale, the resulting Standard Curve B will give a straight line to advantage.

The present invention is described in the above with respect to the determination of an antigen and/or antibody in a sample by applying the latex agglutination phenomenon caused by contacting the antigen and/or antibody in the sample with the sensitized carrier particles (i.e., LA system). The method according to the invention is also suitable for the determination of a sample to which the inhibitory action against the above-mentioned agglutination is applied (i.e., LI system).

Incomplete antigens such as, for example, haptens can be determined by applying the method according to the invention to the LI system.

In this case, for instance, an antigen may be supported on the insoluble carrier particles used in this invention, the sensitized carrier particles are reacted competitively with a given amount of an antibody which has been reacted with an antigen of a predetermined concentration (i.e., a standard antigen solution), and the absorbance or percent absorption of the resulting reaction mixture is measured. The above procedure is repeated at various concentrations of the standard antigen solution to prepare Standard Curve C. Subsequently, an unknown sample is reacted with the same antibody of the definite concentration, and the resulting reaction mixture is then reacted with the sensitized carrier. These reactions should be carried out under substantially the same conditions as in the preparation of Standard Curve C. The absorbance or percent absorption of the final reaction mixture with the sensitized carrier particles is measured and compared with the standard curve (C) to determine the amount (concentration) of the antigen in the unknown sample. Folllowing the procedure of the above-mentioned LI system except that a certain antibody is supported on the insoluble carrier particles, an antibody in an unknown sample can be determined by the LI system. In addition, it is possible, if desired, to support both an antigen and an antibody of different species on the insoluble carrier particles and determine an antigen and an antibody in an unknown sample. Thus, in accordance with the invention, the quantitative measurement of a wide variety of antigens and/or antibodies are possible, for example, (1) blood examination of subjects or blood donors which is indispensable for emergency operations, for example, detection of blood group substances, the Au-or HB-antigen or other contaminants in the blood, or determination of fibrin/fibrinogen degradation products (FDP) which is recently regarded as useful in the convalescent control for kindey transplantation or renal failure patients, (2) determination of human chorionic gonadotropin (hCG) which is regarded as significantly important in the pregnancy diagnosis or the convalescent control of chorioepithelioma, (3) determination of hCG, or urinary estriol glucuronide which is a metabolite of follicular hormone, said determination being required for monitoring pregnancy, (4) determination of oxytocin in blood which is considered to be a uterine contraction inducer, (5) determination of certain adrenal cortical hormones such as corticoids and aldosterone, or adrenocorticotropic hormones (ACTH), (6) determination of insulin for diabetics, or determination of follicle stimulating hormone, luteinizing hormone, estrogens, corpus luteum hormone, etc., (7) determination of gastrin or secretin which is a gastrointestinal hormone, (8) detection and determination of an antibody in the body fluid of patients with allergy, syphilis, or hemolytic streptococcicosis, rubella, autoimmune diseases such as collagen disease and other infection diseases, and the like.

The present invention may be adopted, of course, for the qualitative or semi-quantitative measurement of these antigens and/or antibodies.

The method according to this invention may be carried out, for example, with the following apparatus.

The apparatus useful for the invention involves (a) insoluble carrier particles for supporting an antiody or antigen, said carrier particles having an average diameter of not greater than 1.6 microns, (b) an absorption cell for holding a reaction mixture obtained by reacting the antibody or antigen supported on the insoluble carrier and a corresponding antigen and/or antibody in a liquid medium, said cell having a thickness in the range of 0.5 to 10 mm, (c) an irridiation unit for emitting light which contains rays of polychromatic light having a particular wavelength region in the range of 0.6 to 2.4 microns, (d) a means for applying the irradiation light to the reaction mixture in the absorption cell and sensing the intensity of the polychromatic light of the wavelength region in the range of 0.6 to 2.4 microns which has been transmitted by the reaction mixture, and (e) a means for determining the absorbance or percent absorption of the reaction mixture for the above polychromatic light, said means being operated in response to sensing means (d).

Figure 3:
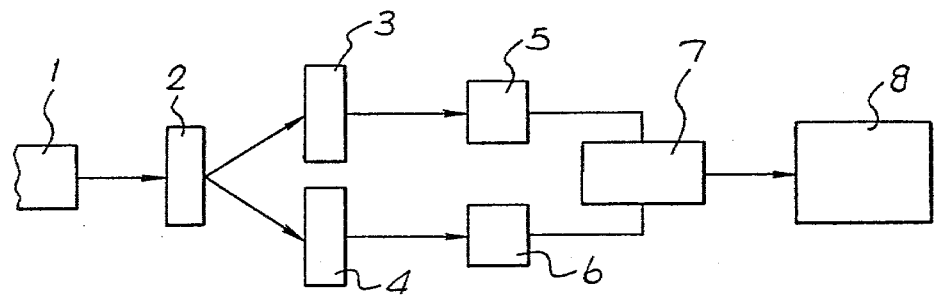
FIG. 3 is a systematic diagram which shows the basic structure of an apparatus useful for this invention.

The above-mentioned measuring apparatus may possess the same basic structure as in the prior art photometric apparatus, except for the essential structural characteristics as described in (a), (b), (c), (d) and (e). Thus, as illustrated in FIG. 3, the basic structure of the apparatus useful for this invention comprises an irradiation unit comprising light source (1) and light filter (2); sample cell (3) for holding a sample for the measurement of an antigen-antibody reaction, and reference cell (4) for holding a control sample for compensation; photocells (5) and (6) for sensing the light transmitted by the respective cells and transforming them into electric signals, amplifier (7) for amplifying the electric signals; and displaying or recording unit (8) for displaying or recorcing the amplified electric signals. As light source (1) any of the above-listed sources may be used. The light emitted from source (1) is, if necessary, filtered through light filter (2) so as to apply a polychromatic light having a particular wavelength region in the range of 0.6 to 2.4 microns, preferably 0.8 to 1.8 microns, and more preferably 0.9 to 1.4 microns to cells (3) and (4). Accordingly, light filter (2) is selected from those capable of effectively filtering polychromatic light of the above wavelength region. For example, a color filter which cuts off rays of wavelength up to 800 nm may be used as light filter (2).

A particular advantage of this invention is that a Ga-As light emitting diode can be used as light source (1). In this preferred embodiment of this invention, various benefits can be attained. For example, the use of an expensive light filter or prism can be avoided, and as a result the cost of production and maintenance of the apparatus can be reduced. In addition, the ditto diode can apply to cells (3) and (4) much more intensive light than filtered irradiation light so that the degree of amplification required of amplifier (7) can be largely decreased.

Alternatively, as previously mentioned, light filter (2) in FIG. 3 may be omitted, in which case the light emitted from source (1) is directly applied to cells (3) and (4), and instead of light filter (2), similar light filters may be interposed between cell (3) and photocell (5) and between cell (4) and photocell (6).

Sample cell (3) and reference cell (4) may be composed of transparent glass or synthetic resin (e.g., acrylic resins) and may generally be a box-shape having a rectangular cross section. The cell thickness may be in the range of 0.5 to 10 mm, preferably 1 to 5 mm. The transmissive windows may advantageously possess at least 30% transmission, preferably 80% or higher transmission for the light of a wavelength region of 0.6 to 2.4 microns.

In sample cell (3) is placed a reaction mixture prepared by reacting an antigen or antibody or a mixture thereof with the corresponding antibody and/or antigen supported on insoluble carrier particles in a liquid medium in such a manner as previously described with respect to the method of this invention. On the other hand, in reference cell (4) is placed a control sample prepared by dispersing only the antibody-and/or antigen-sensitized insoluble carrier particles in the liquid medium.

The light rays transmitted by cells (3) and (4) are received by photocells (5) and (6), respectively, and transformed into electric signals, the respective strength of which is in proportion to the respective intensities of the light received by the cells. As photocells (5) and (6), any type of photocells capable of transducing an intensity of light received into an electric signal having a strength proportional to the intensity of the light may be used. Lead sulfide photoconductive elements and silicon photodiode, for example, may be employed to advantage. The electric signals transformed by the photocells may be amplified by amplifier (7) in a conventional manner and displayed or recorded on indicator or recorder (8) so as to read them visually. If a timer is incorporated in indicator or recorder (8), it is possible to automatically record the absorbance after a predetermined period of reaction time or record the time required to reach a predetermined value of absorbance. In a preferred embodiment of the apparatus useful for this invention, sample cell (3) is equipped with an agitator which may be a mixing rod movable in the cell or a micropropeller rotatable in the cell. By the use of these means, the antigen-antibody reaction between the sample and the sensitized carrier particles can be accelerated while being progressed in substantially fixed conditions, and in addition it is possible to perform quite readily such operation so as to stop the reaction immediately after a predetermined period of reaction time has passed or to accurately read the reaction time elapsed by the time the absorbance reaches a predetermined value.

Having generally described this invention, a more complete understanding can be obtained by reference to certain examples which are provided herein for purposes of illustration only and are not intended to be limiting in any manner.

EXAMPLE 1

(1) Preparation of an anti-hCG-sensitized latex reagent

To 10 ml of a solution of anti-(human chorionic gonadotropin) (anti-hCG) antibody in a glycine buffer (concentration: 2 mg/ml), 1 ml of a polystyrene latex having an average diameter of 0.220 micron (Dow Chemical Co., 10 wt.% solids content) was added, and the mixture was stirred for 30 minutes at room temperature, then warmed to 40° C. and stirred for an additional 30 minutes at this temperature. The mixture was then centrifuged at 12,000 r.p.m. for 50 minutes under cooling at 2° to 4° C. The precipitates were collected by decantation and suspended in a 0.2 wt.% solution of bovine serum albumin so as to prepare an anti-hCG-sensitized latex reagent containing 0.5% by weight of the sensitized latex particles.

(2) Preparation of a calibration curve

Figure 4:
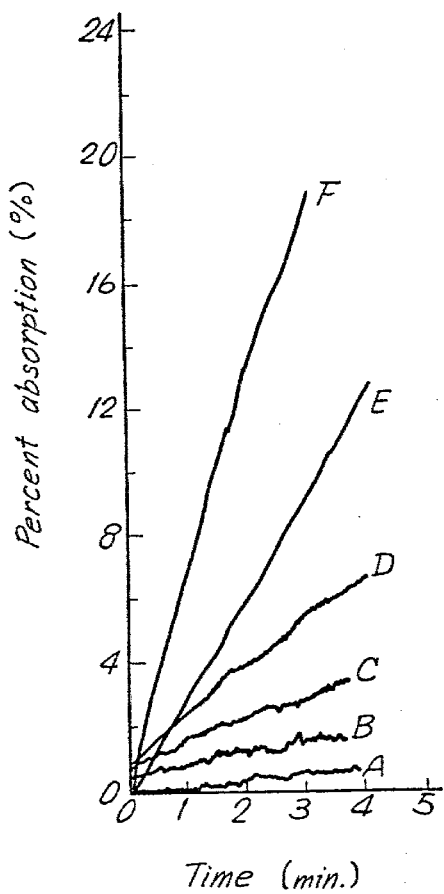
FIG. 4 is a chart which shows the change of percent absorption with time at various concentrations of hCG solutions, wherein anti-hCG-latex particles having an average diameter of 0.200 micron are used and a cell is irradiated with polychromatic light emitted from a tungsten lamp as a light source, said light being free of any spectral component of wavelength of not longer than 0.8 micron by means of a light filter.
Figure 5B:
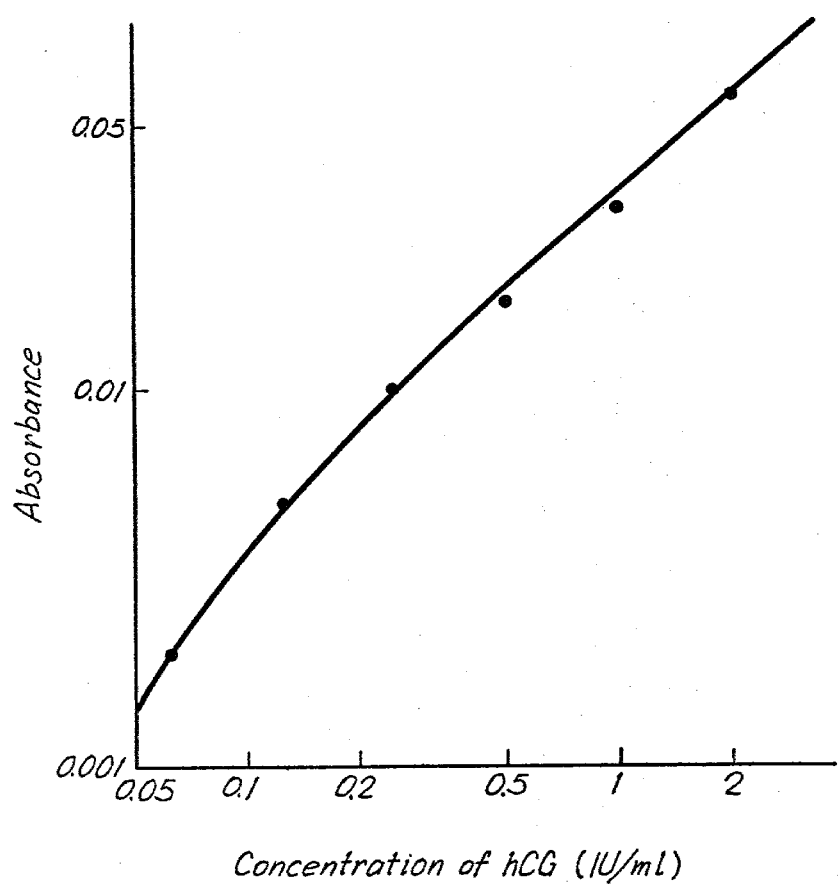
FIG. 5(b) is a calibration curve which shows the change of absorbance after 2-minutes' reaction with concentration of hCG solution, wherein anti-hCG-latex particles having an average diameter of 0.220 micron are used and a cell is irradiated with polychromatic light emitted from a tungsten lamp as a source, said light being free from any spectral component of wavelength not longer than 0.8 micron.

A 0.2 ml aliquot of the anti-hCG-latex reagent prepared in Part (1) above was admixed with 0.2 ml of each standard hCG solution having a concentration indicated in Table-A below (said standard solutions being dissolved in a medium of isotonic sodium chloride solution containing 0.2% by weight of bovine serum albumin) by shaking in a small test tube for 5 seconds. The resulting mixture was immediately transferred to an acrylic resin absorption cell of 2 mm in thickness equipped with an L-shaped stainless steel stirring rod of 1 mm in diameter movable up and down in the cell, and stirring was started at a speed of 160 vibrations per minute. Using a conventional tungsten lamp (12 V, 8 W) as a light source in combination with a light filter (Ditric Optics, D 800), the cell was irradiated with the light which was free of any spectral component having a wavelength not longer than 0.8 micron by means of the filter. The intensity of the light transmitted by the cell was measured with a silicon photocell (Hamamatsu TV, S874-8K) and the change of percent absorption with time was recorded on a pen recorder. The chart thus obtained is shown in FIG. 4, in which the symbols A, B, C, D, E and F are given in the order of increasing concentration of the standard hCG solutions. From FIG. 4, the value of percent absorption after 2 minutes were read off on each curve. The results are summarized in Table-A below, in which the corresponding values of absorbance obtained by calculations are also incorporated. When the data of percent absorption and absorbance in Table-A were plotted against the concentration of hCG, the graphs or calibration curves shown in FIG. 5(a) and FIG. 5(b) respectively, were obtained.

Using these calibration curves, the amount of hCG in an unknown sample can be determined as illustrated in the following Part (3).

Table-A

| Concentration of standard hCG solution (IU/ml) | % Absorption after 2 min. | Absorbance after 2 min. |
|---|---|---|
| 0.0625 | 0.5 | 0.002 |
| 0.125 | 1.2 | 0.005 |
| 0.250 | 2.2 | 0.010 |
| 0.500 | 3.9 | 0.017 |
| 1.00 | 6.6 | 0.030 |
| 2.00 | 12.9 | 0.060 |

() Assay of hCG in unknown samples

A sample of blood or urine was collected from a subject and if the sample was blood, the serum was separated therefrom in the conventional manner. If necessary, the sample was then diluted by the dilution factor indicated in Table-B below. A 0.2 ml aliquot of the undiluted or diluted sample was shaken in a small test tube for 5 seconds together with 0.2 ml of the anti-hCG-latex reagent prepared in the foregoing Part (1).

This procedure was carried out in exactly the same way as described in Part (2) above. Subsequently, the value of percent absorption after 2 minutes was determined in the same manner as described in Part (2) and compared with the calibration curve obtained in Part (2) above to determine the concentration of hCG in the sample. The results are summarized in Table-B below.

For the purpose of comparison, Table-B also involves the data obtained in accordance with the conventional radioimmunoassay (RIA) method (S. M. Ratky et al., Brit. J. Haematol. 30, 145–149, 1975).

Table-B

| Sample No. | Material | Patient's name (Diagnosis) | Dilution factor | % Absorption after 2 min. | hCG concentration in unknown sample (IU/ml) Method of this invention | RIA method |
|---|---|---|---|---|---|---|
| 1 | Urine | K.O. (Hydatid mole) | × 1000 | 5.5 | 750 | 683 |
| 2 | " | K.S. (Malignant teratoma) | × 10 | 6.2 | 8.5 | 8.29 |
| 3 | " | H.S. (Normal, female) | × 1 | <0.3 | <0.03 | 0.018 |
| 4 | Serum | Y.K. (Hydatid mole) | × 1 | 4.4 | 0.63 | 0.543 |
| 5 | " | H.M. (Pregnancy, 10th week) | × 100 | 4.55 | 60.3 | 65.16 |
| 6 | " | A.N. (Lung | × 1 | 2.9 | 0.35 | 0.391 |

Table-B-continued

| Sample No. | Material | Patient's name (Diagnosis) | Dilution factor | % Absorption after 2 min. | hCG concentration in unknown sample (IU/ml) | |
|---|---|---|---|---|---|---|
| | | | | | Method of this invention | RIA method |
| | | cancer) | | | | |

EXAMPLE 2

In a small test tube, 0.2 ml of an anti-hCG-sensitized polystyrene latex reagent (containg 0.5% latex particles with an average diameter of 0.220 micron) which was prepared in exactly the same way as described in Part (1) of Exakmple 1, and 0.2 ml of a standard hCG solution having a concentration indicated in Table-C below were shaken for 5 seconds, and the resulting mixture was irradiated with light from a tunsgsten lamp which was free from any spectral component of a wavelength not longer than 0.8 micron. The irradiation was conducted in the same way as in Part (2) of Example 1. In this example, however, the time required to reach 4% absorption was measured (said time including the 5-second shaking period).

The results are summarized in Table-C.

Table-C

| Concentration of standard hCG solution (IU/ml) | Time required to reach 4% absorption (min.) |
|---|---|
| 0.0625 | 18.0 |
| 0.125 | 10.4 |
| 0.25 | 5 |
| 0.5 | 2.4 |
| 1 | 1.25 |
| 2 | 0.70 |

FIG. 6 shows the graph obtained by plotting the data in Table-C on log-log graph paper with hCG concentration as abscissa and time in minute as ordinate.

Using the graph of FIG. 6 as a calibration curve, it is possible to determine the concentration of hCG in an unknown sample as described in Part (3) of Example 1.

EXAMPLE 3

Following the procedure of Example 1, Part (2) an anti-hCG-sensitized latex reagent prepared in exactly the same manner as described in Example 1, Part (1) was reacted with a standard hCG solution. The apparatus used was identical to that used in Part (2) of Example 1 except that the light filter was omitted. The value of percent absorption after 3 minutes was determined and the results are shown in Table-D.

Table-D

| Concentration of standard hCG solution (IU/ml) | % Absorption after 3 min. |
|---|---|
| 0.0625 | 1.6 |
| 0.125 | 2.6 |
| 0.25 | 3.6 |
| 0.5 | 6.4 |
| 1 | 8.8 |
| 2 | 14.0 |

Figure 7:
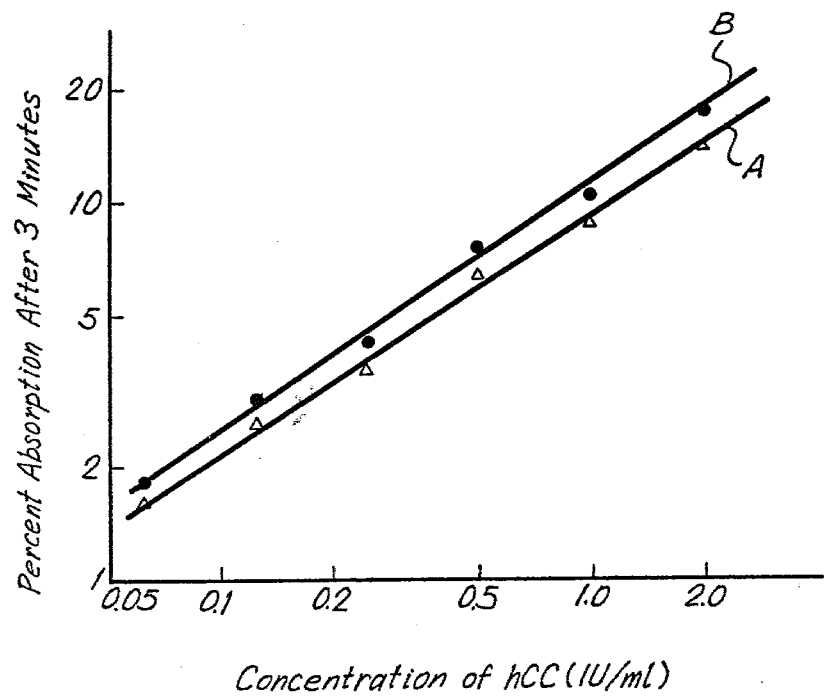
FIG. 7 shows Calibration Curve A which indicates the change of percent absorption with concentration of hCG solution measured by applying the light emitted from a source of tungsten lamp directly to a cell without any light filter, and Calibration Curve B which indicates such a change of percent absorption measured by interposing a light filter between the cell and ditto detector and applying the same light.

When the above data were plotted on log-log graph paper with hCG concentration as abscissa and percent absorption after 3 minutes as ordinate, a clear linear relationship was obtained as shown by Line A in FIG. 7.

Using the calibration curve thus obtained, it is possible to determine hCG in unknown samples.

EXAMPLE 4

An anti-hCG-latex reagent prepared in exactly the same way as described in Example 1, Part (1) was reacted each of standard hCG solutions having various concentrations and the value of percent absorption after 3 minutes was determined. The apparatus was identical to that used in Example 1, Part (2), except that the light filter for the removal of any spectral component having a wavelength of not longer than 0.8 micron was placed between the cell and the detector (photocell) instead of in front of the cell. The results are shown in Table-E.

Table-E

| Concentration of standard hCG solution (IU/ml) | % Absorption after 3 min. |
|---|---|
| 0.0625 | 1.8 |
| 0.125 | 3.0 |
| 0.25 | 4.2 |
| 0.5 | 7.6 |
| 1.0 | 10.4 |
| 2.0 | 17.2 |

When the above data were plotted on log-log graph paper with hCG concentration as abscissa and percent absorption after 3 minutes as ordinate, a clear linear relationship was obtained as shown by Line B in FIG. 7.

Using the cabibration curve thus obtained, it is possible to determine hCG in unknown samples.

EXAMPLE 5

(1) Preparation of an anti-(fibrinogen) antibody-sensitized latex (anti-Fg-latex) reagent To 10 ml of a solution of anti-(human fibrinogen) (Fg) antibody in a glycine buffer (concentration: 2 mg/ml), 0.5 ml of a polystyrene latex having an average diameter of 0.109 microns (Dow Chemical Co., 10 wt.% solids content) and 0.5 ml of another polyptyrene latex having an average diamter of 0.234 micron (ditto) were added, and the mixture was stirred for 30 minutes at room temperature then warmed to 40° C. and further stirred for an additional 30 minutes at this temperature. Thereafter the mixture was centrifuged at 12,000 r.p.m. for 50 minutes under cooling at 2° to 4° C. The precipitates were collected by decantation and then suspended in a 0.2 wt.% solution of bovine serum albumin so as to prepare an anti-Fg-sensitized latex reagent containg 0.50% by weight of the anti-Fg-sensitized latex particles.

(2) Preparation of a calibration curve

A 0.2 ml aliquot of the anti-Fg-sensitized latex reagent prepared as above was admixed with a standard Fg solution having a concentration indicated in Table-F below by shaking for 5 seconds, and immediately thereafter the resulting reaction mixture was processed using the same apparatus as described in Example 1, Part (2). Thus, the reaction mixture was irradiated with light from a tungsten lamp which was free from any spectral component having a wavelength of not longer than 0.8 micron while being stirred with a stirring rod moving up and down, and the time required to reach an absorbance of 0.05 was measured.

The results are shown in Table-F.

Table-F

| Concentration of standard Fg solution (μg/ml) | Time required to reach 0.05 in absorbance (min.) |
| --- | --- |
| 0.125 | 13.2 |
| 0.25 | 4.0 |
| 0.5 | 1.25 |
| 1.0 | 0.50 |
| 2.0 | 0.20 |

Figure 8:
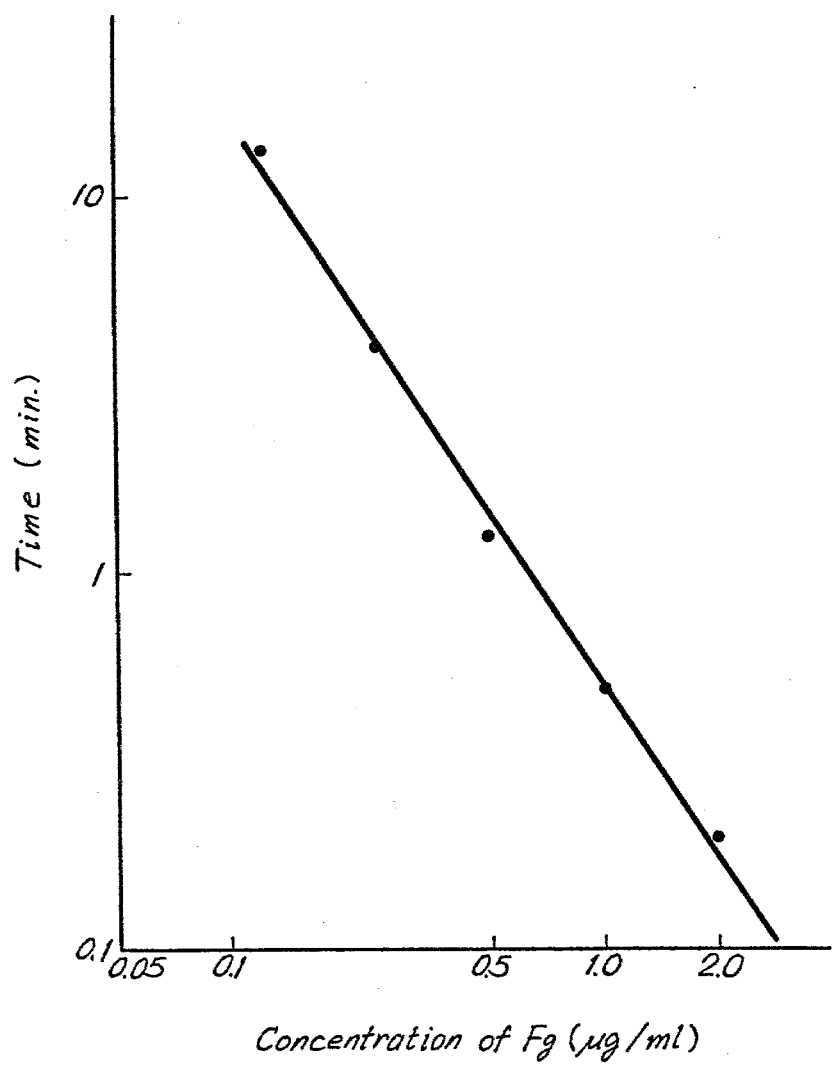
FIG. 8 is a calibration curve represented in terms of time required to reach an absorbance of 0.05, wherein an anti-Fg-sensitized latex reagent is reacted with a standard Fg solution and the cell is irradiated with light from a tungsten lamp which is free from any spectral component having a wavelength of not longer than 0.8 micron.

When the above data were plotted with Fg concentration as abscissa and time required to reach an absorbance of 0.05 as ordinate, a linear relationship was obtained as shown in FIG. 8.

EXAMPLE 6

A 0.15 ml aliquot of an anti-hCG-latex (average diameter: 0.220 micron) reagent (latex content: 0.25%) prepared in the same manner as described in Example 1, Part (1) and 0.15 ml of a standard hCG solution (in an isotonic sodium chloride solution containing 0.2 wt.% bovine serum albumin) having a concentration indicated in Table-G below were placed in a small test tube and shaken for 5 seconds to thoroughly admix them.

Immediately thereafter, the mixture was transferred to an acrylic resin cell of 4 mm in thickness equipped with a stirrer having a rotary blade of 2.4 mm in diameter and the percent absorption was continuously recorded under stirring at a speed of 1,200 r.p.m. The light source was a Ga-As ditto diode (Monsanto Co., Model ME-7124; peak emission wavelength 940 nm; half width 50 nm) and the light emitted from the source was directly applied to the cell. The intensity of the light transmitted by the cell was measured with a silicon photocell (Hamamatsu TV, S874-8K). The value of percent absorption after 4 minutes from the commencement of the stirring was read from the record, and converted to the corresponding value of absorbance, which was plotted against the concentration of standard hCG solution, resulting in a graph as shown in FIG. 9. Using the graph of FIG. 9 as a calibration curve, it is possible to determine hCG in unknown samples as illustrated in Example 1 Part (3).

Table-G

| Concentration of standard hCG solution (IU/ml) | % Absorption | Absorbance |
| --- | --- | --- |
| 0.078 | 8.8 | 0.041 |
| 0.156 | 14.9 | 0.071 |
| 0.312 | 23.8 | 0.118 |
| 0.625 | 39.0 | 0.215 |
| 1.25 | 59.5 | 0.393 |

EXAMPLE 7

An anti-hCG-sensitized polystyrene latex reagent (0.5% by weight content of the latex particles) was prepared in the same way as described in Example 1, Part (1) except for the use of a mixture of polystyrene latices having average diameters of 0.109 micron and 0.220 micron.

A 0.2 ml aliquot of the anti-hCG-sensitized latex reagent thus obtained and 0.2 ml of a standard hCG solution having a concentration indicated in Table-H below were mixed in a micro test tube and immediately processed with the same apparatus as used in Example 1, Part (2). Thus, the reaction mixture was irradiated with light from a tungstan lamp from which any spectral component having a wavelength of not longer than 0.8 micron has been removed. The absorbance after 6 minutes was dtermined and the results are given in Table-H.

Table-H

| Concentration of standard hCG solution (IU/ml) | Absorbance after 6 min. |
| --- | --- |
| 0.2 | 0.010 |
| 0.4 | 0.024 |
| 0.6 | 0.038 |
| 0.8 | 0.050 |
| 1.0 | 0.058 |

Figure 10:
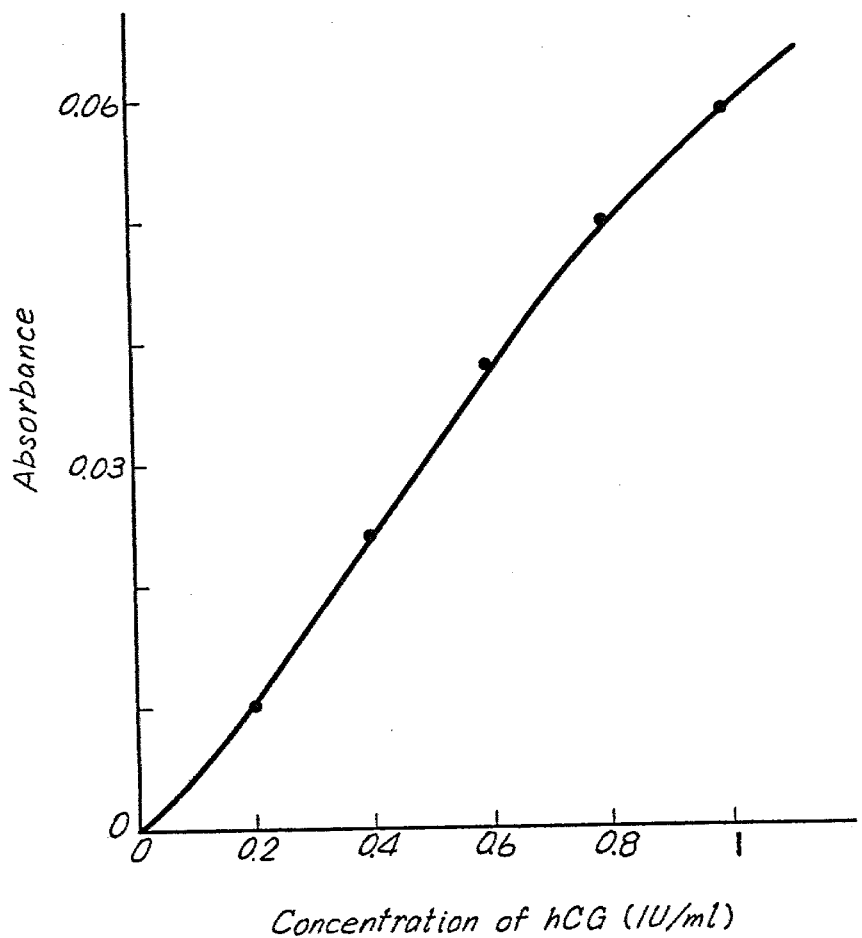
FIG. 10 is a calibration curve for absorbance measured by irradiating a cell containing an reaction mixture of an anti-hCG sensitized latex reagent and a standard hCG solution with the light emitted from a tungsten lamp which is free from any spectral component having a wavelength of not longer than 0.8 micron.

When the above data were plotted with concentration of standard hCG solution as abscissa and absorbance after 6 minutes as ordinate, a calibration curve as shown in FIG. 10 was obtained.

EXAMPLE 8

In a small test tube, 0.1 ml of an anti-hCG-sensitized latex reagent (containing 0.33 wt.% latex particles) as prepared in Example 1, Part (1) and 0.1 ml of a standard hCG solution having a concentration indicated in Table-I below were admixed by shaking for 5 seconds. Immediately thereafter, the reaction mixture was transferred to an acrylic resin absorption cell of 4 mm in thickness equipped with a stirrer having a rotary blade of 2.4 mm in diameter, and irradiated with a continuous polychromatic light of a radiant peak wavelength of 0.95 micron and a half width of 0.03 micron which was obtained by a combination of a tungsten lamp as a light source and a prism-type monochrometer. The percent absorption after 4 minutes was determined and the results are summarized in Table-I.

Table I

| Concentration of standard hCG solution (IU/ml) | % Absorption after 4 min. |
| --- | --- |
| 0.0625 | 8.0 |
| 0.125 | 11.0 |
| 0.25 | 20.0 |
| 0.50 | 31.7 |
| 1.0 | 47.8 |

Figure 11:
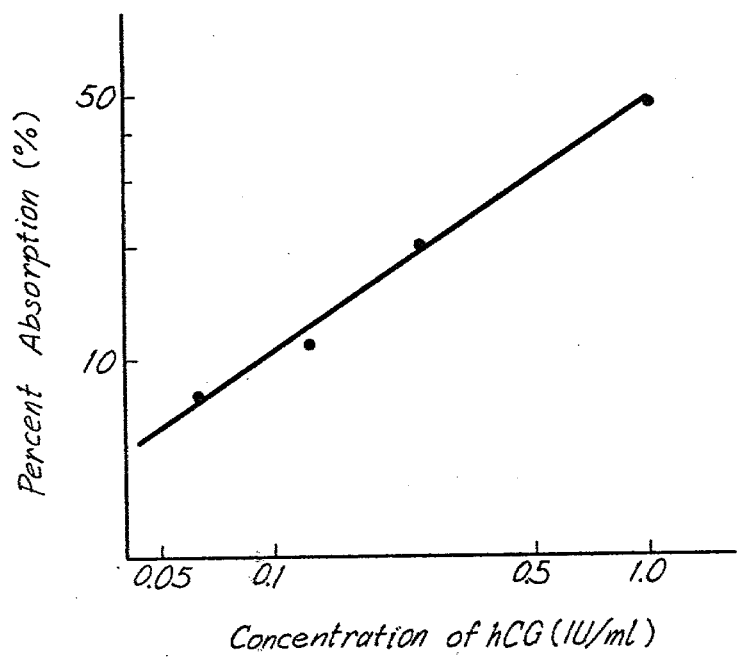
FIG. 11 is a calibration curve which indicates the absorbance after 4-minutes' reaction of an anti-hCG sensitized latex reagent and a standard hCG solution measured at a wavelength of 0.95 micron with a half width of 0.03 micron.

When the above data were plotted on log-log graph paper with concentration of standard hCG solution as abscissa and percent absorption after 4 minutes as ordinate, a cabibration curve as shown in FIG. 11 was obtained.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. An absorbance method of measuring antigens and antibodies comprising reacting an antigen or antibody or a mixture thereof with the corresponding antibody or antigen or mixture thereof, which has been supported on insoluble carrier particles having an average diameter of not greater than 1.6 microns to sensitize the carrier particles, said reaction being carried out in a liquid medium and the concentration of said carrier particles in the resulting mixture being 0.05 to 1% by weight; irradiating the reaction mixture with light which contains rays of polychromatic light having a particular wavelength region in the range of 0.6 to 2.4 microns and so selected that, when applied to the reaction mixture, it gives an increase in absorbance or percent absorption with time; and measuring the absorbance or percent absorption of the reaction mixture for the polychromatic light.

2. The method according to claim 1 wherein the irradiating light is composed predominantly of the rays of polychromatic light of wavelengths in the range of 0.6 to 2.4 microns which, when applied to the reaction mixture, gives an increase in absorbance or percent absorption with time.

3. The method according to claim 1 or 2 wherein the polychromatic light has wavelengths in the range of 0.8 to 1.8 microns.

4. The method according to any one of claims 1 or 2 wherein the irradiating light is substantially free from rays of wavelengths shorter than 0.8 micron.

5. The method according to any one of claims 1 or 2 wherein the polychromatic light has a half width or wavelength range of at least 0.03 micron.

6. The method according to any one of claims 1 or 2 wherein the polychromatic light has a half width or wavelength range of at least 0.05 micron.

7. The method according to claim 1 wherein the reaction mixture is irradiated with light which contains rays of polychromatic light having a particular wavelength region in the range of 0.6 to 2.4 microns and so selected that, when applied to the reaction mixture, it gives an increase in absorbance or percent absorption with time, and the light transmitted by the reaction mixture is filtered, thereby the measurements of absorbance or percent absorption being taken only for the polychromatic light.

8. The method according to claim 1 wherein the polychromatic light consists essentially of rays having wavelengths longer than the average diameter of the carrier particles by a factor of at least 1.1.

9. The method according to claim 1 wherein the polychromatic light consists essentially of rays having wavelengths longer than the average diamter of the carrier particles by a factor of at least 1.5.

10. The method according to claim 1 wherein the insoluble carrier particles have an average diameter in the range of 0.1 to 1.0 micron.

11. The method according to claim 1 wherein the insoluble carrier particles have an average diameter in the range of 0.2 to 0.8 micron.

12. The method according to claim 1 wherein the carrier particles consists essentially of fine powder of an organic high molecular substance or an inorganic substance which is substantially insoluble in the liquid medium.

13. The method according to claim 12 wherein the fine powder of the organic high molecular substace is fine powder of a synthetic resin, bacteria or cell membrane fragments.

14. The method according to claim 12 wherein the fine powder of the organic high molecular substance is particles of a polystyrene latex.

15. The method according to claim 12 wherein the fine powder of the inorganic substance consists of at least one member selected from metals, inorganic oxides and minerals.

16. The method according to claim 12 wherein the fine powder of the inorganic substance consists of silica, alumina or silica-alumina.

17. The method according to claim 1 wherein the reaction between the antigen or antibody or a mixture thereof and the insoluble carrier particles supporting the corresponding antibody or antigen or mixture thereof is carried out under such conditions as to accelerate contact of the carrier particles with each other as much as possible.

18. The method according to claim 1 wherein the reaction between the antigen or antibody or a mixture thereof and the insoluble carrier particles supporting the corresponding antibody or antigen or mixture thereof is carried out under, substantially fixed conditions which accelerate contact of the carrier particles with each other.

19. The method according to claim 17 or 18 wherein the reaction is carried out with agitation.

20. The method according to claim 1 wherein as antigen or antibody or mixture thereof a test fluid is reacted with the corresponding antibody or antigen or mixture thereof supported on the carrier particles for a given period of time under, substantially fixed conditions, and the absorbance or percent absorption of the resulting reaction mixture is measured to determine the concentration of the antigen or antibody or mixture thereof in the test fluid.

21. The method according to claim 1 wherein an antigen and/or antibody in a test fluid is reacted with the corresponding antibody or antigen or mixture thereof supported on the carrier particles under, substantially fixed conditions, and the concentration of the antigen or antibody or mixture thereof in the test fluid is determined by measuring the length of time required to increase the absorbance or percent absorption of the reaction mixture to a given value.

22. The method according to claim 1 wherein the carrier particles are used in such a proportion that the concentration of the carrier particles in the reaction mixture is 0.1 to 0.6% by weight.

23. The method according to claim 1 wherein the liquid medium is selected from water or a mixture of water and a water-miscible organic solvent.

24. The method according to claim 1 wherein an antigen- or antibody-containing test fluid which may be diluted or concentrated is reacted with a suspension of the carrier particles supporting the corresponding antibody or antigen.

25. The method according to claim 1 wherein a test fluid containing an antibody or antigen to be determined is reacted first with the corresponding antigen or antibody and the reaction mixture is then reacted with a suspension of the carrier particles supporting the corresponding antibody or antigen.

26. The method according to claim 1 wherein the antibody or antigen is supported on the insoluble carrier particles by physical or chemical adsorption or a mixture of both thereon.

27. The method according to claim 1 wherein the antibody or antigen is supported on the insoluble carrier particles by chemical bonding through a coupling agent.

* * * * *